United States Patent
Starchevich

(10) Patent No.: US 6,341,757 B1
(45) Date of Patent: Jan. 29, 2002

(54) FLOW REGULATOR

(76) Inventor: Jovanka Starchevich, 138 Sullivan ST., New York, NY (US) 10012

( * ) Notice: Subject to any disclaimer, the term of this patent is extended or adjusted under 35 U.S.C. 154(b) by 0 days.

(21) Appl. No.: 09/624,664

(22) Filed: Jul. 25, 2000

Related U.S. Application Data

(63) Continuation-in-part of application No. 09/319,456, filed as application No. PCT/US97/21617 on Nov. 25, 1997, now abandoned, and a continuation-in-part of application No. 08/759,438, filed on Dec. 5, 1996, now Pat. No. 5,718,409

(60) Provisional application No. 60/150,538, filed on Aug. 25, 1999.

(51) Int. Cl.[7] ............................................. F16K 7/06
(52) U.S. Cl. ..................................................... 251/6
(58) Field of Search ........................................ 251/6

(56) References Cited

U.S. PATENT DOCUMENTS

| 3,297,558 A | 1/1967 | Hillquist |
| 3,625,472 A | 12/1971 | Rychlik |
| 3,685,787 A | 8/1972 | Adelberg |
| 4,013,263 A | 3/1977 | Adelberg |
| 4,047,694 A | 9/1977 | Adelberg |
| 4,475,709 A | 10/1984 | Becker, Jr. |
| 4,725,037 A | 2/1988 | Adelberg |
| 4,974,811 A | 12/1990 | Ishida |
| 5,014,962 A | 5/1991 | Adelberg |
| 5,190,079 A | * 3/1993 | Nakada ..................... 138/45 |
| 5,718,409 A | * 2/1998 | Starchevich ................. 251/6 |

* cited by examiner

*Primary Examiner*—John Fox
(74) *Attorney, Agent, or Firm*—Howard C. Miskin; Gloria Tsui-Yip

(57) ABSTRACT

A flow regulator has a pair of side walls extending generally parallel to one another, a bottom wall connecting the side walls to one another and defining an elongate channel for receiving a compressible tube, a roller rotatably and shiftably mounted to the side walls for rolling along the tube in the channel and compressing the tube against the bottom wall. The bottom wall is provided with a formation which varies from a first end of the channel towards an opposite, second end thereof, whereby compressive force applied to the tube via the roller is different at different longitudinal positions of the roller along the channel. A bracket or bow-shaped bridge is disposed about or between the side walls at one end of the channel. The bracket is in contact with outer surfaces of the side walls only in regions of the side walls spaced from the bottom wall. The bracket or bridge are advantageously made with less inherent stiffness than the assembly defining the elongate channel.

22 Claims, 3 Drawing Sheets

FLOW REGULATOR

CROSS-REFERENCE TO RELATED APPLICATION

This application is a continuation-in-part of provisional application No. 60/150,538 filed Aug. 25, 1999 and of application Ser. No. 09/319,456 filed as a U.S. national phase of international patent application No. PCT/US97/21617 which was filed Nov. 25, 1997 as a continuation-in-part of application Ser. No. 08/759,438 filed Dec. 5, 1996, now U.S. Pat. No. 5,718,409.

FIELD OF THE INVENTION

This invention relates to a flow regulator. More particularly, this invention relates to a flow regulator of the type which compresses a tube to vary a flow rate of a fluid passing through the tube. Even more particularly, this invention relates to a flow regulator of the roller type. The invention is useful in medical applications, to control the flow rate of intravenous fluids, parenteral fluids, blood, plasma, etc.

BACKGROUND OF THE INVENTION

Intravenous tubes have been widely used for supplying nutrients and medication to patients. Most existing manually adjustable clamps for regulating the flow rate through an intravenous tube have a high degree of inaccuracy, particularly after the clamped tubing has been in use for a period of time in excess of one hour. In addition, existing manually actuated clamps cannot be used where the fluid being delivered through the tubing is viscous, for example, blood. If a substantial degree of accuracy in flow rate maintenance is required, it has been necessary to utilize an expensive pump system. Even pumps systems are limited in their accuracy.

A particularly common kind of flow regulator in medical applications is the so-called Adelberg clamp which uses the combination of an inclined plane or V-grooved surface and a roller that is moved along the inclined plane or grooved surface to variably compress the tube to allow more or less liquid to flow through the tube. Although widely used, the Adelberg clamp is less than ideally accurate and reliable, so as to require continual monitoring and adjustment to maintain a desired flow rate. The position of the roller is easily shifted in the V-grooved and ramped versions since the clamp design has not taken into consideration the direct effect of stress and strain as a critical contributing factor in maintaining an accurate and consistent flow rate through the roller clamp.

OBJECTS OF THE INVENTION

An object of the present invention is to provide an improved manually adjustable flow regulator of the above-described roller type.

Another object of the present invention is to provide a manually adjustable flow regulator which has enhanced accuracy and reliability.

An additional object of the present invention is to provide such a flow regulator which is inexpensive and easy to manufacture.

A further object of the present invention is to provide a manually adjustable flow regulator which is utilizable where a medical fluid is to be delivered through a flexible tube.

These and other objects of the present invention will be apparent from the descriptions and illustrations herein. It is believed that each of the above-described objects is achievable in one or more embodiments of the invention described herein.

BRIEF DESCRIPTION

A flow regulator comprises, in accordance with the present invention, a pair of side walls extending generally parallel to one another, a bottom wall connecting the side walls to one another and defining an elongate channel for receiving a compressible tube, a roller rotatably and shiftably mounted to the side walls for rolling along the tube in the channel and compressing the tube against the bottom wall. The bottom wall is provided with a formation which varies from a first end of the channel towards an opposite, second end thereof, whereby a compressive force applied to the tube via the roller is different at different longitudinal positions of the roller along the channel. A reinforcement bracket is disposed about the side walls at one end of the channel. The bracket is in contact with outer surfaces of the parallel side walls only in regions of the side walls spaced from the bottom wall. In a different embodiment, the bracket is replaced with a bridge of relatively flexible construction spanning the two side walls, disposed at the flow regulator shut off end. Advantageously, the side walls and a bottom wall, including all parts of the clamp with the exclusion of the bracket or bridge, are made from a material more rigid than the material from which the bracket or bridge is made.

As suggested above, prior V-grooved or ramped roller clamps suffer from setpoint drift attributable to shifting of the roller position. The prior clamp structures are not believed to have taken into adequate consideration the direct effect of stress or strain as a critical contributing factor in degrading an accurate flow rate performance of the roller clamp. The relationship of a stiffness of the bridge to the flow regulator chamber or channel walls, as well as the contributory factor of differences in intrinsic elasticity of the materials used for component manufacture are critical in maintenance of accurate device performance. The present invention describes an effective method of taking cognizance of stress and strain in the device, and controlling these factors for optimum performance.

U.S. Pat. No. 5,718,409 to the same inventor implicitly dealt with stress and strain in a roller clamp by introducing a reinforcing bracket to an existing design. In further tests of similar devices it has become evident that modifying the flexibility or stiffness relationships between the chamber walls and the bridge or bracket component further improved the accuracy and consistency of the device, by limiting the flexing of the side walls and simultaneously reducing a strain state of the bridge or bracket.

U.S. Pat. No. 5,718,409, the disclosure of which is incorporated herein, shows a bracket contacting the outer surface of the sidewalls of the roller clamp body at a shut-off or maximally restricted flow end of the device. In the prior art, the roller tended to roll towards the shut off end during operation of the clamp. The movement is presumed to have arisen as an effect of operating stresses in the interrelated parts of the roller clamp assembly. As the roller pinches the tube, pressure is generated on the plastic walls of the device. This pressure causes an end of the clamp to flair open to various degrees, depending on a position of the roller. In order to control the effect of stress on the device, structure defining the roller clamp chamber requires a more rigid material construction. The elastic relationship of the roller clamp chamber structure—comprising parallel side walls and bottom wall—to the bracket or bridge structure is an important design parameter, as the two parts structure interact to accommodate the varying stresses resulting from different roller setting in the operating device.

The bracket previously described in U.S. Pat. No. 5,718,409 serves to maintain flow constancy by controlling a change in a gap distance between the parallel side walls of the roller clamp, engaging the walls predominantly at the shut off end. Simultaneously, the bracket provides the side walls with a controlled springy effect which means that, as the roller starts to roll towards the shut off end, the controlled springy flexibility of the walls will respond to the roller's tendency to roll down; at times when the amount of fluids delivered lessen, it would cause a decrease in the degree of stress and strain between the bracket and the chamber, and the pressure between the roller and the tube where the roller might otherwise change its position, with bracket feature on the clamp the roller will be held constant by the springy effect of the parallel side walls. After this discovery was initially made by the inventor by numerous in-house tests and several official laboratory tests, improvements were made in the design which make this device easier and less expensive to manufacture, while maintaining the original objectives of maintaining superior and constant flow regulating. These improvements result in a device having a predetermined and controlled elastic performance relationship during stress effects which involve the entire assembly.

The bracket or bridge is preferably disposed at the end of the flow regulator where the tube is subjected to the greatest compressive forces and the controlled flow rate is the lowest. The bracket prevents an undue flexing of the side walls away from each other under forces exerted by the roller and the compressed tube. In one version or embodiment of the present invention, the bracket mounts around the parallel side walls and the bottom wall connecting the parallel sides. In another version, the bracket fits over the parallel side walls only, at the shut off end of the clamp. In yet another version, the bracket is mounted in such a manner that it interfaces with the bottom wall and the side walls and the bracket clips over the top edge of the side walls, leaving a section of a gap between the parallel side walls open. The thickness of the bracket ends is sufficient to stop the roller from accidentally rolling past the end of the channel housing.

In accordance with a feature of the present invention, it is contemplated that the side walls at the bracketed end of the channel are connected to one another only by the bottom wall at one side and the bracket at an opposite side. Thus, a web or strut which extends between the side walls at the low-flow-rate end of a conventional regulator is omitted.

The bracket is made of a less rigid material, or exhibits less stiffness or resistance to bending, than the walls of the flow regulator chamber or channel. In another version or embodiment of the present invention, the bridge, also made of a less rigid material than the bottom wall and sides walls of the roller clamp, is disposed between the side walls at the shut off end of the flow regulator. This bridge has a curved formation of a bow like structure. This convex formation of the bridge points away from the shut off end and in opposite direction from the open end of the flow regulator.

Pursuant to another feature of the invention, the bracket includes portions spaced from the side walls in a region about the bottom wall.

In a specific embodiment of the present invention, the bracket is substantially U-shaped, with legs having free ends provided with fingers contacting the bottom wall. The fingers are substantially collinear and oriented towards one another.

In accordance with a further feature of the present invention, the side walls are provided along inwardly facing surfaces with respective grooves, the roller having a pair of shaft elements extending laterally in opposing directions along an axis of the roller, each of the shaft elements being provided at a free end with a friction enhancing formation. The friction enhancing formation may take the form of knurling, a layer of high friction material, embedded grit particles, or a series of axially extending ridges and interleaved longitudinal grooves.

In accordance with a yet another feature of the present invention, the flow regulator further comprises a pointer member coupled with the roller to move therewith as the roller negotiates the channel. A series of marks are disposed along the outer surface of one of the side walls for cooperating with the pointer to provide an indication of flow rate.

In accordance with an additional feature of the present invention, at least one of the sidewalls is provided with a seat receiving the bracket. The seat may be defined by a recess in the side wall or a shoulder on the side wall. The seat assists in retaining the bracket on the regulator.

The bracket may be bonded to one or both of the side walls, for example, by ultrasonic welding.

In a specific embodiment of the invention, the reinforcement bracket includes a first U-shaped portion spanning the channel on a side thereof opposite the bottom wall of the flow regulator and disposed in contact with outer surfaces of the side walls only in regions of the side walls spaced from the bottom wall. In this embodiment, the reinforcement bracket further includes a second U-shaped portion partially surrounding the first U-shaped portion, the second U-shaped portion having legs extending generally parallel to and spaced from the side walls of the flow regulator, the legs having free ends provided with fingers disposed in contact with the first U-shaped portion.

A manually adjustable flow regulator in accordance with the present invention provides substantially enhanced accuracy and reliability. The improved performance results from the addition of a single part to existing roller-type clamps. Accordingly, the flow regulator of the present invention is inexpensive and easy to manufacture. A manually adjustable flow regulator in accordance with present invention is utilizable where a medical fluid, for example, a parenteral solution, saline, plasma or blood, is to be delivered through a flexible tube.

In another feature of the present invention, it has been determined by experimentation that an unexpected benefit is accrued in terms of flow stability if the pair of side walls and bottom wall defining the elongate channel are manufactured utilizing material and dimensions creating a relatively stiff profile, while the bracket is manufactured using material and dimensions resulting in a relatively flexible reinforcing bracket or clip anchoring the side walls. Since one of ordinary skill in the art would likely have thought it desirable to make all components as stiff as possible to limit shifting of the roller, the relative advantage of a less stiff bridge or bracket part is an unexpected result.

An improvement made here over U.S. Pat. No. 5,718,409 accordingly originates in an observation that the rigidity or flexibility relationship between the chamber walls and the bracket (or bridge) is a significant feature in controlling performance of the flow clamp device. In specific embodiments of the present invention, the bridge or bracket is more flexible in its structure than the roller clamp chamber housing.

In accordance with a further feature of the present invention, the side walls and the bottom walls are made of a substantially less flexible material than the bracket or convex bridge are made of.

A manually adjustable flow regulator in accordance with the present invention provides an enhanced accuracy and reliability. The improved performance results from a substantially rigid chamber housing and a less rigid bracket or bridge assembly in a roller-type clamp. By incorporating these improvements a flow clamp device will prove easier and less expensive to manufacture, while yet advantageously maintaining desirable critical features of the device previously disclosed in the referenced patent, the matter of which is incorporated herein.

Figure 2:
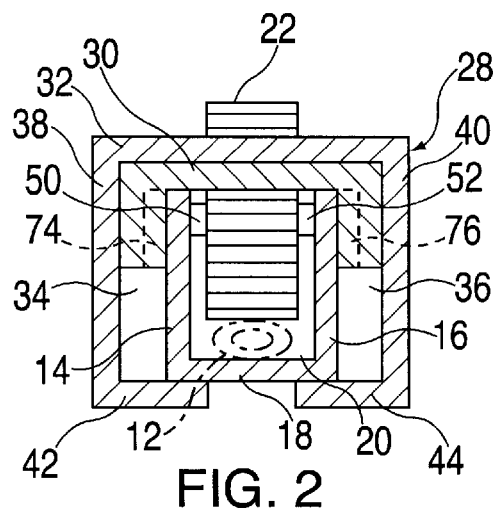
FIG. 2 is a transverse cross-sectional view, on a larger scale, taken along line II—II in FIG. 1.
Figure 7:
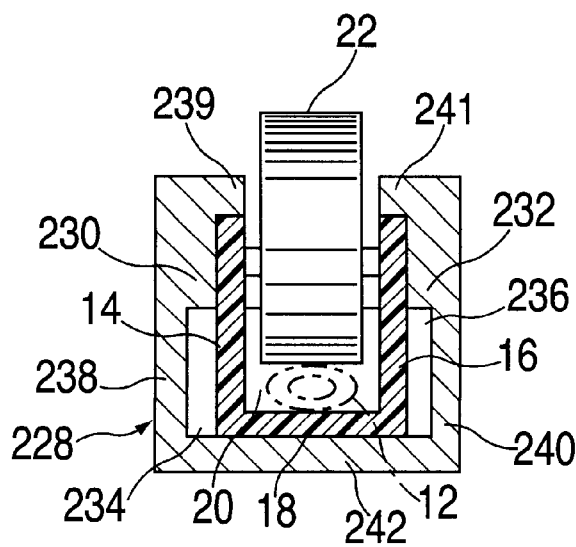
FIG. 7 is a transverse cross-sectional view, similar to FIGS. 2 and 6, showing another alternative construction for the invention.
Figure 8:
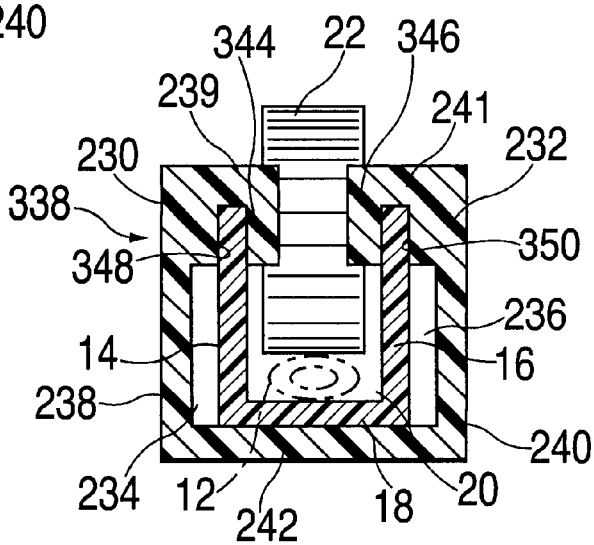
FIG. 8 is a transverse cross-sectional view, similar to FIGS. 2, 6 and 7, showing yet another alternative construction for the invention.
Figure 6:
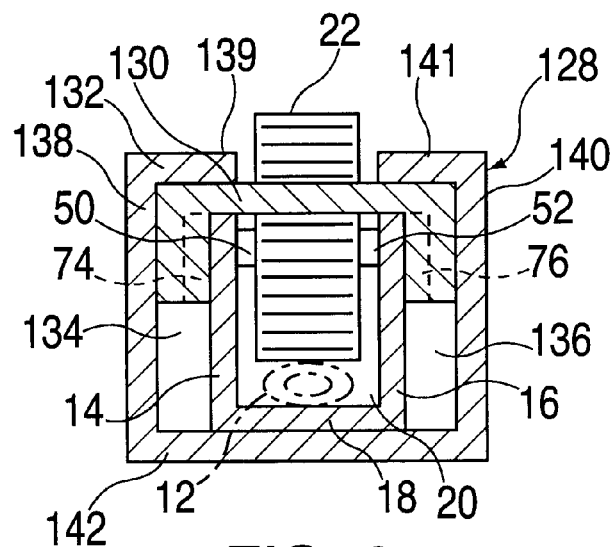
FIG. 6 is a transverse cross-sectional view, similar to FIG. 2, showing an alternative construction for the invention.

Where structures in FIGS. 6, 7 and 8 are identical to structures in FIG. 2, the same reference designations are used. Where structures of FIG. 7 are repeated in FIG. 8, reference designations are also repeated.

DESCRIPTION OF THE PREFERRED EMBODIMENTS

The drawings illustrate a flow regulator 10 intended for use with a compressible medical feed tube 12. The tube can deliver saline, blood, plasma, total parenteral fluids and other liquids to a patient, for example, to a blood vessel of the patient. Regulator 10 has a pair of side walls 14 and 16 which extend generally parallel to one another. A bottom wall 18 extends substantially the length of side walls 14 and 16 and connects the side walls to one another to define an elongate channel 20 for receiving tube 12. Channel 20 is generally open towards one side, as indicated at 21 in FIG. 3.

A roller 22 is rotatably and shiftably mounted to side walls 14 and 16. Roller 22 is partially disposed in channel 22 and partially extends through opening 21 for enabling the manual application of a torque to roller 22. Roller 22 is in frictional engagement with tube 12 for rolling along the tube in channel 20, under the manual application of torque, and compressing tube 12 against bottom wall 18. Bottom wall 18 is provided with a conventional formation such as a ramp (not shown) and/or a tapered V-shaped groove (not shown) which has a shape varying from a first end 24 of regulator 10 (and channel 20) towards an opposite, second end 26 thereof. Thus, compressive force applied to tube 12 via roller 22 is different at different longitudinal positions of roller 22 along channel 20.

A bracket assembly 28 is disposed about side walls 14 and 16 at the one end 26 of channel 20. End 26 is that terminal portion of flow regulator 10 where tube 12 is subjected to the greatest compressive forces and the controlled flow rate is the lowest. Bracket assembly 28 serves to prevent an undue flexing of side walls 14 and 16 away from one another under the forces exerted by roller 22 and compressed tube 12. This bracing action of bracket assembly 28 limits side wall flexing at virtually all longitudinal positions of roller 22 along channel 20.

Bracket assembly 28 is in contact with outwardly facing surfaces (not labeled) of side walls 14 and 16 only in regions thereof spaced from bottom wall 18. More particularly, bracket assembly 28 includes an inner U-shaped bracket element 30 and an outer U-shaped bracket element 32. Bracket elements 30 and 32 may be a unitary injected molded polymeric piece or two separate polymeric pieces joined by ultrasonic or heat welding before or after assembly to side walls 14 and 16. Inner bracket element 30 engages side walls 14 and 16 only along free edges and outer surfaces thereof spaced from bottom wall 18. Outer bracket member 32 surrounds inner bracket element 30, as well as side walls 14 and 16 and bottom wall 18. Outer bracket element 32 is spaced from side walls 14 and 16 by virtue of inner bracket element 20. In particular, there are gaps 34 and 36 between outer bracket element 32 and side walls 14 and 16 in region about bottom wall 18.

Figure 3:
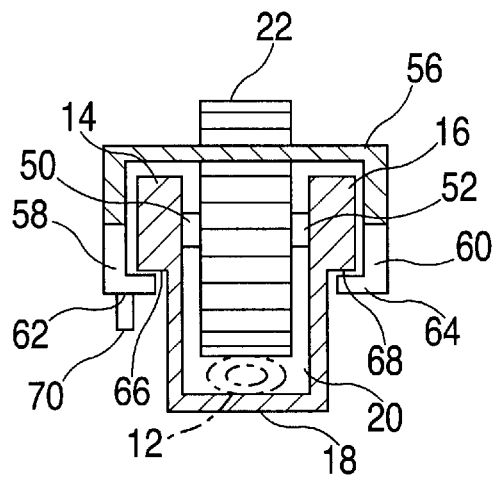
FIG. 3 is a transverse cross-sectional view, on a similarly large scale, taken along line III—III in FIG. 1.

As shown in FIG. 3, side walls 14 and 16 at the bracketed end 26 of regulator 10 and channel 20 are connected to one another only by bottom wall 18 at one side and bracket assembly 28 at an opposite side. There is no web or strut extending between side walls 14 and 16 at the low-flow-rate end 26 as there is in conventional flow regulators.

Outer bracket element 32 has legs 38 and 40 having free ends provided with fingers 42 and 44 which are in contact with bottom wall 18. Fingers 42 and 44 are substantially collinear and oriented towards one another.

Figure 5:
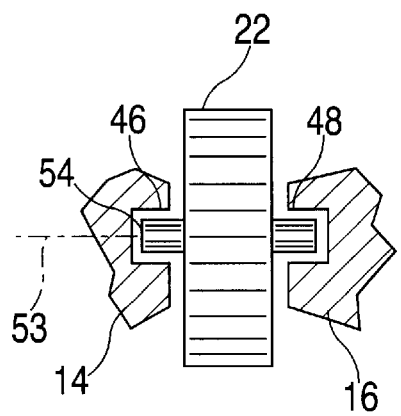
FIG. 5 is a front view of the roller of FIG. 1 and a pair of axle members, showing the axle members projecting into tracks or grooves in side walls of the flow regulator.

Side walls 14 and 16 are provided along inwardly facing surfaces (not labeled) with respective grooves 46 and 48 (FIG. 5) as in conventional intravenous flow regulators. Roller 22 has a pair of axle or shaft elements 50 and 52 extending laterally in opposing directions along an axis 53 of roller 22. Each shaft element 50 and 52 is provided at a free end with friction enhancing longitudinal ridges 54 defined by interleaved longitudinal grooves (not separately labeled). The friction enhancing function of ridges 54 may be performed by other formations such as knurling, a layer of high friction material, or embedded grit particles.

Figure 1:
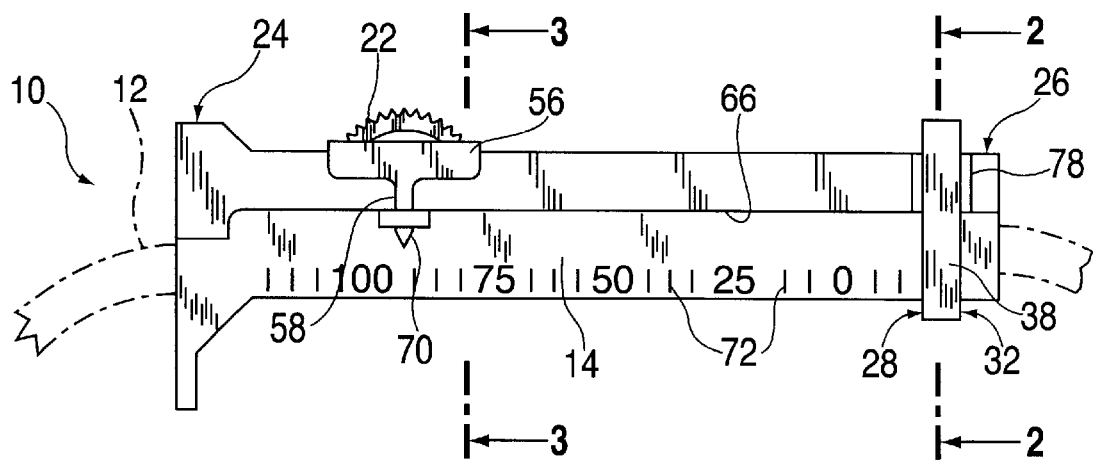
FIG. 1 is a side elevational view, on an enlarged scale, of an intravenous flow regulator in accordance with the present invention.
Figure 4:
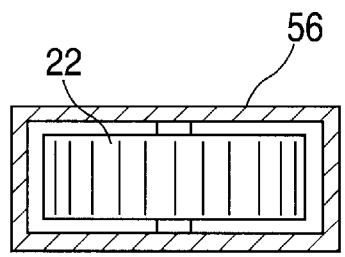
FIG. 4 is a top plan view of a roller member and a slidable frame entrained thereto, both shown in FIG. 1.

As illustrated in FIGS. 1, 3 and 4, flow regulator 10 is provided with a rectangular frame 56 traversed by roller 22. Frame 56 is entrained to roller 22 to travel therewith along channel 20. Frame 56 has one or two arms 58 and 60 which extend generally in parallel along respective side walls 14 and 16 and which are provided at free ends with inwardly turned hooks 62 and 64. Hooks 62 and 64 engage respective longitudinally extending shoulders 66 and 68 on side walls 14 and 16 to thereby anchor frame 56 to the side walls of the flow regulator. A pointer member 70 projecting from one arm 58 is coupled via frame 56 to roller 22 to move therewith as the roller negotiates channel 20. A series of marks 72 are disposed along the outer surface of side wall 14 for cooperating with pointer 70 to provide an indication of flow rate.

As shown in FIG. 2, side walls 14 and 16 are formed with respective recesses 74 and 76 which define seats receiving inner bracket element 30. Recesses or seats 74 and 76 assist in retaining the bracket assembly 28 on regulator side walls 14 and 16. More specifically, side walls 14 and 16 have stops or lips 78 (see FIG. 1) at regulator end 26 for preventing the bracket assembly 28 from sliding off the flow regulator. This feature is particularly useful where bracket assembly 28 is retrofitted to a pre-existing flow regulator. In addition, bracket assembly 28 may be bonded to one or both side walls 14 and 16, for example, by ultrasonic welding.

A flow regulator as described herein has been tested using a McGaw 1000 cc D5W plastic IV solution bag, a standard McGaw 87 inch microdrip (60 gtts) IV tubing, and a 19 gauge 1½ inch metal needle. The test was conducted at a temperature of 75° F., a drip chamber height of 36 inches above an infusion site, and a flow regulator height of 5 inches below the bottom of the drip chamber. During a test period of four hours, a count of 30 drops was made every thirty minutes with an extra count at ten minutes after the initial count. The time in seconds for counting thirty drops was recorded at each count. The difference in seconds from the initial count and the percent change were calculated and recorded. The average change in the 30 drop time over the four hour period was 0.81 seconds and the average percent changes was 0.31%.

As illustrated in FIG. 6, an alternative construction for the roller clamp assembly particularly at the one end 26 (FIG. 1) of channel 20, includes a bracket assembly 128 disposed about side walls 14 and 16. Bracket assembly 128 is designed to decrease, reduce or eliminate undue flexing of side walls 14 and 16 away from one another under the forces exerted by roller 22 and compressed tube 12. This bracing action of bracket assembly 128 limits side wall flexing at virtually all longitudinal positions of roller 22 along channel 20.

Bracket assembly 128 is in contact with outwardly facing surfaces (not labeled) of side walls 14 and 16 only in regions thereof spaced from bottom wall 18. More particularly, bracket assembly 128 includes an inner U-shaped bracket element 130 and an outer U-shaped bracket element 132. Bracket elements 130 and 132 may be a unitary injected molded polymeric piece or two separate polymeric pieces joined by ultrasonic or heat welding before or after assembly to side walls 14 and 16. Inner bracket element 130 engages side walls 14 and 16 only along free edges and outer surfaces thereof spaced from bottom wall 18. Outer bracket member 132 surrounds inner bracket element 130, as well as side walls 14 and 16 and bottom wall 18. Outer bracket element 132 is spaced from side walls 14 and 16 by virtue of inner bracket element 130. In particular, there are gaps 134 and 136 between outer bracket element 132 and side walls 14 and 16 in region about bottom wall 18.

In the embodiment of FIG. 6, as in the embodiment of FIG. 2, side walls 14 and 16 at the bracketed end 26 of regulator 10 and channel 20 are connected to one another only by bottom wall 18 at one side and bracket assembly 128 at an opposite side. There is no web or strut extending between side walls 14 and 16 at the low-flow-rate end 26 as there is in conventional flow regulators.

Outer bracket element 132 has legs 138 and 140 having free ends provided with fingers 139 and 141 which are in contact with inner bracket element 130. Fingers 139 and 141 are substantially collinear and oriented towards one another. At ends opposite fingers 139 and 141, legs 138 and 140 are connected to one another by a bight member 142 which is in contact with bottom wall 18.

In contrast to bracket 28, bracket 128 extends 360° about channel 20.

As depicted in FIG. 7, another alternative construction for the roller clamp assembly includes a substantially U-shaped bracket 228 disposed about side walls 14 and 16. As in other constructions of the roller clamp assembly discussed herein, bracket 228 is designed to decrease, reduce or eliminate undue flexing of side walls 14 and 16 away from one another under the forces exerted by roller 22 and compressed tube 12. This bracing action of bracket 228 limits side wall flexing at virtually all longitudinal positions of roller 22 along channel 20.

Bracket 228 is in contact with outwardly facing surfaces (not labeled) of side walls 14 and 16 only in regions thereof spaced from bottom wall 18. Bracket 228 substantially surrounds side walls 14 and 16 and bottom wall 18. Bracket 228 includes a pair of legs 238 and 240 spaced along their lower portions (not separately designated) from side walls 14 and 16 by gaps 234 and 236.

In the embodiment of FIG. 7, side walls 14 and 16 at the bracketed end 26 of regulator 10 and channel 20 are connected to one another only by bottom wall 18, as reinforced by bracket 228. As in other embodiments of a roller-type flow regulator described herein, there is no web or strut extending between side walls 14 and 16 at the low-flow-rate end 26.

Legs 238 and 240 have thickened free ends 230 and 232 which contact outer surfaces of side walls 14 and 16 at ends thereof spaced from bottom wall 18. Fingers 239 and 241 at the tips of legs 238 and 240 extend over the free ends of side walls 14 and 16 and cooperate therewith to attach bracket 228 to regulator 10 in a snap-lock fit. Fingers 239 and 241 are substantially collinear and oriented towards one another. At ends opposite fingers 239 and 241, legs 238 and 240 are connected to one another by a bight member 242 which is in contact with bottom wall 18.

As depicted in FIG. 8, a modified alternative construction for the roller clamp assembly includes a substantially U-shaped bracket 328 disposed about side walls 14 and 16. Bracket 328 is substantially identical to bracket 228 except that bracket 328 includes flanges 344 and 346 connected to ends of fingers 239 and 241. Flanges 344 and 346, together with thickened ends 230 and 232, define slots 348 and 350 which receive free ends or edges of side walls 12 and 14. Thus, bracket 328 is more firmly locked to flow regulator 10.

To comprehend a feature of roller clamp embodiments described below with reference to FIGS. 9 through 13, a concept of bending modulus will be introduced. For the purposes of this disclosure, a bending modulus is defined as a force divided by an angular deviation of a structure. In particular, the bending modulus of a portion of a roller clamp comprising side walls and a bottom wall will be taken as a force exerted on a defined location on the side walls tending to separate those sidewalls divided by a resulting angular deviation from parallelism of inside surfaces of the sidewalls, assumed not to deviate significantly from parallel in an unstressed rest configuration. The modulus is assumed to be measured at small displacements, within a realm of linear elasticity of all components subject to flexure. In this case the modulus may be assumed to be additive, that is, equal to a sum of forces on various components which would be exerted separately, acting at the same location to achieve an identical displacement in the individual components (carried if necessary by fictitious components in an event that a point of application resides in a particular component). To emphasize that a bending modulus in a second component may be measured additively with that of a first component, with an assumption of linearity, that is, that the modulus so measured is identical to that which would be measured by replacing the first component by a "phantom" or stress-free intermediate, the modulus of the second component may be referred to as an "effective bending modulus". An "effective bending modulus" when used in this application shall be construed to be synonymous with a "bending modulus". When it is desired to emphasize a location and plane of operation of the bending modulus, the bending modulus previously defined may also be described as about the longitudinal axis of the channel, in a body formed by the side walls and bottom walls. Since only one bending modulus is considered in connection with this disclosure, any of the above given descriptions of bending moduli shall be deemed synonomous. A motivation of this description in characterizing a feature of the present invention will become more readily understood hereinbelow.

The bending modulus may be measured in any consistent system of units, since a feature of the invention will be characterized by an inequality, and not by an absolute value of the modulus. In particular, a further feature of invention will be characterized by a value of the bending modulus measured at the sidewalls adjacent to top surfaces thereof, and adjacent to a location of a reinforcing bracket or clip, and further in particular by a relation of the bending modulus measured at this fixed location with no bracket or clip in place, and with a reinforcing bracket or clip in place. The invention is ideally characterized by an increment of the bending modulus with the clip in place which is smaller than the existing bending modulus. A meaning of this requirement may be understood by the additivity of moduli in the realm of small displacements, or linear elasticity, as discussed above. In effect, an increment in bending modulus by addition of a reinforcing clip or bracket is the same as an independent value of a bending modulus of the bracket in a similar configuration, with forces carried by "phantom" parts (since a point of application of the force is not directly on the bracket). In a most simple sense, the bracket or clip is less stiff than a surrounding structure. To reiterate, ideally a reinforcing clip or bracket is less stiff, i.e. more flexible, than a remaining structure of the invention, and this situation is more carefully characterized by a requirement on a measurement of a bending moment, as defined and motivated above. The definition and required inequality may course be taken as a condition of a preferable mode of the present invention without reference to a justification or motivation thereof, which is included as an aid to understanding the invention.

The bending moment is taken to be a measure of an angular deviation of inner surfaces of the side walls from parallelism under an action of a force in a defined location. The angular deviation is to be measured in an identical location, or particularly in a transverse or cross-sectional plane at this identical location.

Ideally, for reasons of mechanical stability and reproducibility of flow, a deviation of the inner surfaces of the side walls from parallelism will be substantially constant over a length of the flow clamp. In particular, a variation in angular separation of the walls over a longitudinal dimension or length of the clamp will ideally be no more that 10%. Still more ideally, a variation in an angular deviation of the inner surfaces of the sidewalls over a length of the clamp in the present invention will be no greater than 5%. It will be understood that these percentages express ratios of angles, and thus are free of units.

A colloquial description of a requirement that an angular deviation of the side walls preferably vary by less than 10% over a length of the invention, and yet more preferably or ideally by less than 5%, is that the walls are longitudinally stiff or rigid. For present purposes, when the walls are said to be "longitudinally stiff", this shall be construed to represent the specific requirement described in the above given percentages. The given percentage requirements are to apply to a flow control device over a full range of flows or tube compressions. A full range of tube compressions shall mean from an uncompressed state to a complete occlusion. A standard hospital IV drip tube shall be used in establishing this standard. The side walls are designed to be longitudinally stiff under application of forces generated by a compressed tube and a roller by a suitable choice of side wall thickness, and also a bottom wall thickness in relation to sidewall thickness. Given the stiffness requirement, material dimensioning is a straightforward engineering problem for one skilled in the art, or solved empirically by prototyping.

A mechanism for an improvement in roller clamp function as result of the requirement of longitudinal stiffness or rigidity, i.e., a mechanism for increasing flow stability in a roller clamp as described herein, is thought to lie in maintaining substantial parallelism of the walls. In particular, it may be understood that as the side walls deviate from parallelism, a compressive force is exerted on spindles or axles attached to a roller trapped therebetween. If the side walls are parallel, this force will tend to increase a frictional force between axles and walls and beneficially trap an axle at a fixed location. However, if the walls are substantially flexible, and deviate from parallel, the compressive force will have a longitudinal component tending to force the axles to move along a length of the side walls. The axles and roller may thereby over time creep from an initially set position, a phenomenon which is likely to be aided by jostling or movement of a flow clamp, or by moisture on an exposed mechanism of a flow clamp, conditions which are not unlikely in a patient care setting. Alternatively, a roller setting may be disturbed by peristaltic action of the flowing fluid in the tube. In this case, a roller will tend to drift in setting towards one end of the device.

An alternative mechanism of roller drift in a flow-control roller clamp is that insufficiently rigid wall components may creep plastically, or relax, tending at first to increase drip flow as pressure is relieved on the tube, then decrease flow as the roller drips towards the cut off end under peristaltic action. In practice, it is found that drift effects towards rather than away from the cut-off end typically predominate in the prior art.

The aforesaid condition on relative bending moments in turn facilitates a maintenance of parallelism of the inner walls, while allowing a degree of constraint of angular separation of the sidewalls under compressive forces. It may be comprehended that a reversal of relative bending moments; a relatively stiff reinforcing bracket engaging relatively a relatively flexible clamp body, or side walls and bottom wall, would tend to lead to pinching of the body of the clamp, and a deviation from parallelism; the concept of relative stiffness in bending having again been more carefully defined above, an explanation of an efficacy of these conditions in maintain flow accuracy again being by way of an aid to understanding.

Advantageous conditions of longitudinal stiffness and relative bending moments may be incorporated into any previously described embodiment of the invention. Those skilled in the art will readily comprehend that stiffness and bending are elastic effects which may be modified by choice of material and by thickness of material. However, a further series of embodiments of reinforcing brackets or clips is represented in FIG. 9 et seq., informed by these specific considerations.

Figure 9:
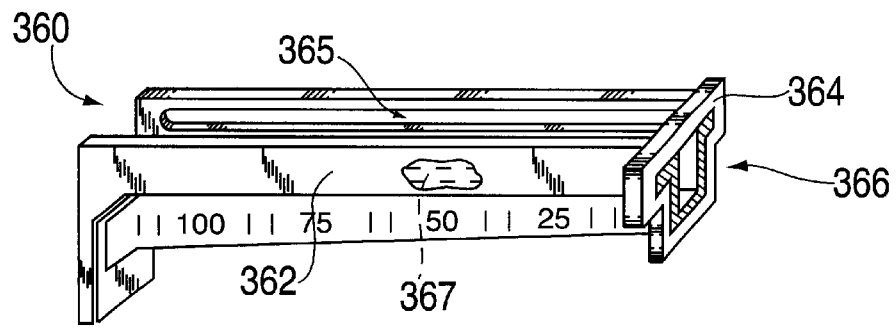
FIG. 9 is a schematic perspective view of alternative embodiment of the present invention, showing a mounting of an end cap or clip.
Figure 10:
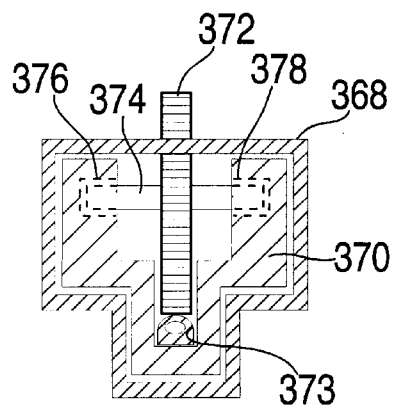
FIG. 10 is a cross-sectional view including a clip similar to the clip of FIG. 9.

A partial flow assembly 360 is shown in FIG. 9, having a body element 362. The body element is provided with internal tracks 365, 367 for engagement of axles 374 of roller 372 (FIG. 10). A reinforcing clip or bracket 364 is disposed on an end 366 of body 362; it can be seen in this embodiment that a top portion of sidewalls (not separately designated) of body 362 have been cut away or notched in a region to receive clip 364. It may be perceived that, because of a closed shape of clip 364, the clip is preferably manufactured of an elastomeric material in order to maintain an effective ratio of bending moduli, as discussed above. Clip 364, as well as the corresponding clips of FIGS. 10–12, may be advantageously snapped into place subsequent to a setting of roller 372, in fixing a flow rate. This sequence of operations allows an easy setting of roller position, followed by a mechanical locking step. Alternatively, the clips may be pre-assembled to the clamp body, and the roller positioned by means of a firmer thumb pressure.

FIG. 10 shows a modification of the embodiment of FIG. 9, in cross section, with a clip 368 in place on an un-notched clamp body 370. Clip 368 may be described as being in contact with a full outer circumference of body 370. Clip 368 and those in FIGS. 9, 11, 12 may be held in place by way of detents (not shown) as a means of snapping-into-place. FIG. 10 also shows greater mechanical detail of the flow clamp, showing roller 372 mounted on axle 374, affixed in tracks 376, 378. The roller is shown partially compressing a drip tube 373.

Figure 11:
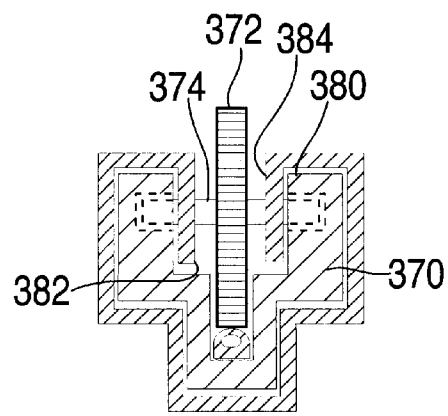
FIG. 11 shows an alternative embodiment of the clip of FIG. 10.

An alternative style of clip or clip-lock 380 is shown in FIG. 11, being open or generally U-shaped in shape rather than closed, and having flanges 382, 384 adapted to slip into an internal channel (not separately designated) of body 370. Clip 380 may be described as being in contact with a full outer circumference of body 370, with flanges protruding into a reentrant portion or channel of the body. Because of the open shape, it may be perceived that clip 380 may be manufactured of a relatively stiff material, such as stainless steel. The open shape only requires a given flexibility in bending in order to maintain a design ratio of bending moments, discussed above, as opposed to a deformation in tension required of closed-shape clip 368.

Figure 12:
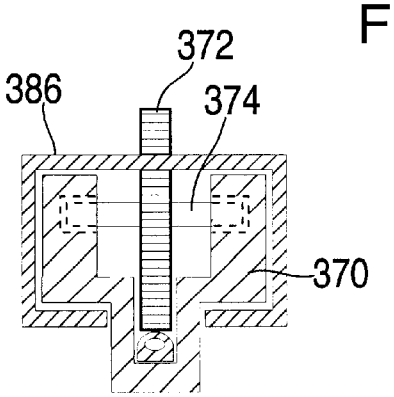
FIG. 12 shows yet an alternative embodiment of the clip of FIG. 10.

A further open-shape clip 386 is shown in FIG. 12; it may be seen that in contrast to clip 380, open on a top, clip 386 is open on a bottom portion. Clip 386 may also be manufacture advantageously of spring steel or stainless steel. Of course a greater thickness of plastic may be used to achieve an equivalent ratio of bending moduli. It may also be noted from FIGS. 10 through 12 that a greater thickness of material is shown in sidewalls (not separately designated) than in a bottom wall, or channel containing tube 373. While partially to accommodate tracks 376, 378, this greater thickness may also be appreciated to contribute to an advantageous longitudinal stiffness to clamp body 370.

Figure 13:
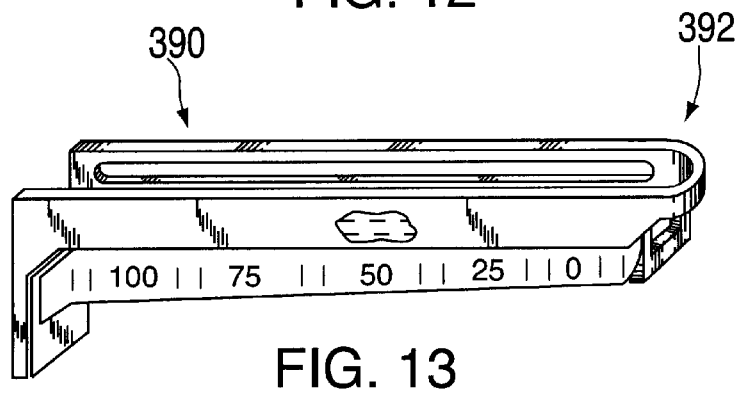
FIG. 13 is a schematic perspective view of yet a further embodiment of the present invention, employing a bow or bridge.

As a final embodiment, a clamp body 390 shown in FIG. 13 incorporates a bridge or bow 392 as a reinforcing element in lieu of a bracket or clip. This bridge is similar in construction to struts closing a clamp body near an end of greater flow constriction in the prior art. While such struts were located close to a position of maximum stress, it may be appreciated now how a straight strut would contribute a much higher effect bending moment than the sidewalls, hence fail to meet the bending moment condition, hence tend to overcome longitudinal stiffness of the clamp body. In other words, since the strut could not stretch, the sidewalls of the clamp may be expected inevitably to bend when a roller was pushed into a restricted end of the channel. The bow or bridge shape of 392 will however provide a greater degree of flexibility in angular deviation of the walls as compared to a straight strut.

Although the invention has been described in terms of particular embodiments and applications, one of ordinary skill in the art, in light of this teaching, can generate additional embodiments and modifications without departing from the spirit of or exceeding the scope of the claimed invention. For example, frame or carriage 56 may take different forms, the function of pointer 70 may be performed by arm 58, and recesses or seats 74 and 76 may be replaced by beads or other stop elements on side walls 14 and 16.

Also, it is to be understood that inner bracket 30 may be used alone, without outer bracket 32, to perform the functions of bracket assembly 28. In that event, bracket 30 is preferably bonded to flow regulator side walls 14 and 16, whether by adhesive and/or ultrasonic welding or other technique. Where bracket assembly 28 is retrofitted to a pre-existing flow regulator 10, outer bracket 32 may be held onto inner bracket by friction, adhesive and/or stop 78.

Accordingly, it is to be understood that the drawings and descriptions herein are proffered by way of example to facilitate comprehension of the invention and should not be construed to limit the scope thereof.

What is claimed is:

1. A flow regulator comprising:
   a pair of side walls extending generally parallel to one another;
   a bottom wall connecting said side walls to one another and defining an elongate channel for receiving a compressible tube;
   a roller rotatably and shiftably mounted to said side walls for rolling along the tube in said channel and compressing the tube against said bottom wall, said bottom wall being provided with a formation which varies from a first end of said channel towards an opposite, second end thereof, whereby compressive force applied to said tube via said roller is different at different longitudinal positions of said roller along said channel; and
   a bracket disposed about said side walls at one end of said channel, said bracket being in contact with outer surfaces of said side walls, said bracket being formed separately from said side walls and said bottom wall.

2. The flow regulator defined in claim 1 wherein said bracket is in contact with said outer surfaces of said side walls only in regions of said side walls spaced from said bottom wall.

3. The flow regulator defined in claim 2 wherein said bracket includes portions spaced from said side walls in a region about said bottom wall.

4. The flow regulator defined in claim 3 wherein said bracket is substantially U-shaped with legs having free ends provided with fingers contacting said bottom wall.

5. The flow regulator defined in claim 4 wherein said side walls at said one end of said channel are connected to one another only by said bottom wall at one side and said bracket at an opposite side.

6. The flow regulator defined in claim 1 wherein said bracket is substantially U-shaped.

7. The flow regulator defined in claim 6 wherein said bracket has legs with free ends provided with substantially collinear fingers oriented towards one another.

8. The flow regulator defined in claim 1 wherein said side walls at said one end of said channel are connected to one another only by said bottom wall at one side and said bracket at an opposite side.

9. The flow regulator defined in claim 1 wherein said side walls are provided along inwardly facing surfaces with respective grooves, said roller having a pair of shaft elements extending laterally in opposing directions along an axis of said roller, each of said shaft elements being provided at a free end with a friction enhancing formation.

10. The flow regulator defined in claim 9 wherein said friction enhancing formation is a series of axially extending ridges.

11. The flow regulator defined in claim 1, further comprising a pointer member coupled with said roller to move therewith as said roller negotiates said channel, also comprising a series of marks disposed along the outer surface of one of said side walls for cooperating with said pointer to provide an indication of flow rate.

12. The flow regulator defined in claim 1 wherein at least one of said sidewalls is provided with a seat receiving said bracket.

13. The flow regulator defined in claim 12 wherein said seat includes a groove in said one of said sidewalls.

14. The flow regulator defined in claim 1 wherein the bracket is disposed at an end of the flow regulator where the tube is subjected to the greatest compressive forces and the controlled flow rate is the lowest.

15. The flow regulator defined in claim 1 wherein said bracket includes a first U-shaped portion spanning said channel on a side thereof opposite said bottom wall and disposed in contact with said outer surfaces of said side walls only in said regions of said side walls spaced from said bottom wall, said bracket further including a second U-shaped portion partially surrounding said first U-shaped portion, said second U-shaped portion having legs extending generally parallel to and spaced from said side walls, said legs having free ends provided with fingers disposed in contact with said first U-shaped portion.

16. The flow regulator defined in claim 1 wherein the bracket is made from a material more flexible than that of the side and bottom walls.

17. The flow regulator defined in claim 1 wherein the bracket is in contact with a full outer circumference of the side walls and the bottom wall.

18. The flow regulator defined in claim 17 wherein the bracket includes a pair of flanges protruding into the channel.

19. The flow regulator defined in claim 1 wherein the bracket has a smaller effective bending modulus about the longitudinal axis of the channel than a body defined by the side walls and bottom wall.

20. The flow regulator defined in claim 1 wherein the side walls are of sufficient longitudinal rigidity to deviate by no more than 10% from parallel over a full range of compression of a standard IV tube.

21. The flow regulator defined in claim 20 wherein the side walls are of sufficient longitudinal rigidity to deviate by no more that 5% from parallel over a full range of compression of a standard IV tube.

22. The flow regulator defined in claim 21 wherein the bracket has a smaller effective bending modulus about the longitudinal axis of the channel than a body defined by the side walls and bottom walls.

* * * * *